ROSE PLANT
Filed Jan. 16, 1974
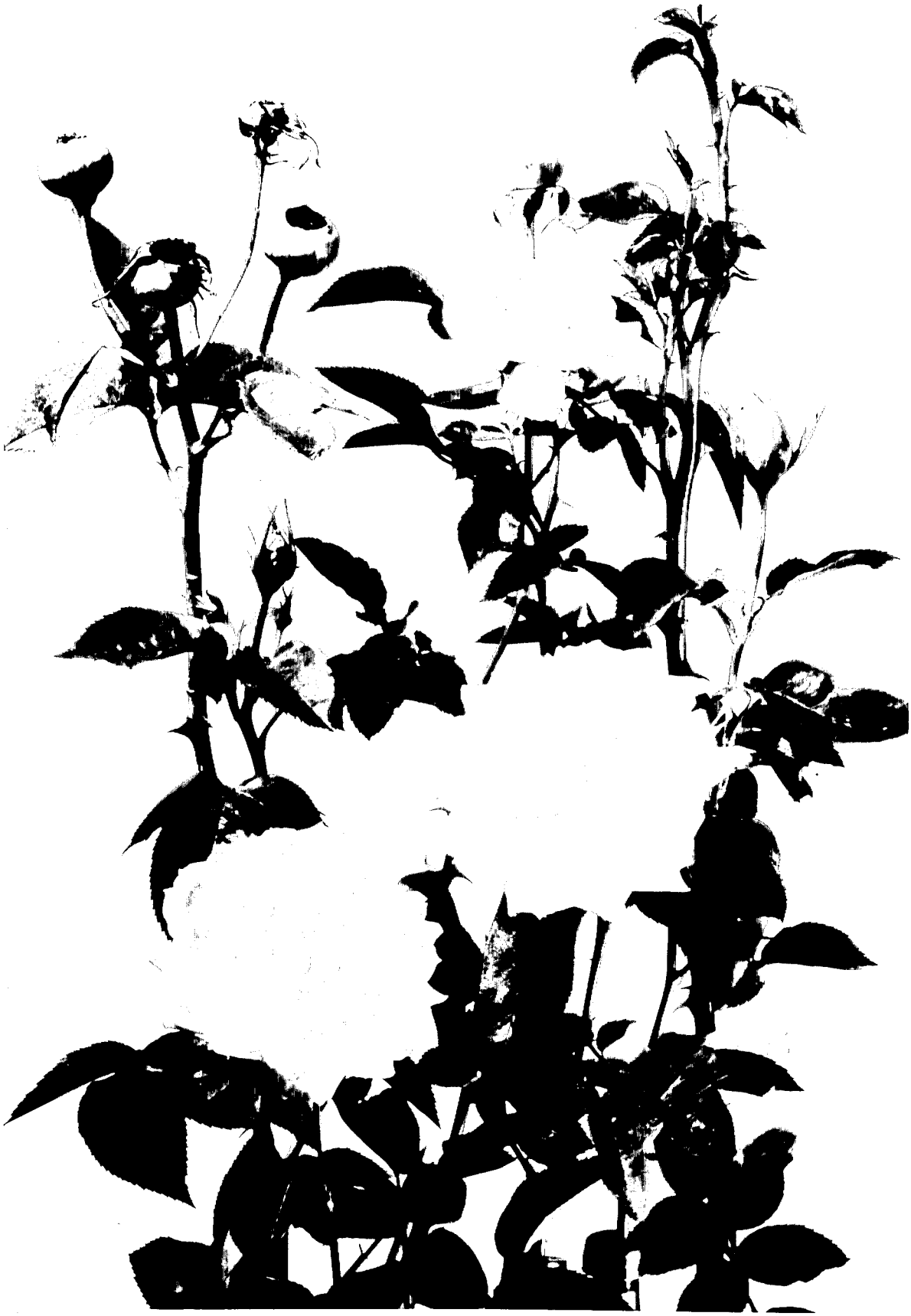

United States Patent Office

Plant Pat. 3,794
Patented Oct. 14, 1975

3,794

ROSE PLANT

Olaf Soenderhousen, Hoersholm, Denmark, assignor to Armstrong Nurseries, Inc., Ontario, Calif.

Filed Jan. 16, 1974, Ser. No. 433,924
Int. Cl. A01h 5/00
U.S. Cl. Plt.—16 1 Claim

ABSTRACT OF THE DISCLOSURE

An outdoor bush-type hybrid rose plant of the grandiflora class, used primarily for garden decoration. The flower has a strong orange color when newly opened, which later turns to a complex of colors, chiefly pink, with shades of yellow, red and orange, intermingled. Its relatively slight fragrance is between that of musk and tea.

The plant itself is vigorous and upright, and moderately branched. It blooms continuously, and is somewhat more resistant to mildew than comparable varieties grown under the same conditions.

This invention relates to a new variety of grandiflora rose. The plant is a seedling of the outdoor bush type, cultivated for garden decoration primarily. It was propagated by Ingenioer O. Soenderhousen in Hoersholm, Denmark, having as its seed parent "Folie d'Espagne" and, as its pollen parent, an unnamed seedling, "Zambra × Danish Pink." It holds its distinguishing characteristics through succeeding propagations by budding. The plant herein described was propagated and grown in Ontario, Calif., from budwood supplied by the originator.

The new variety bears its flowers usually three to five, or more, to a stem, in an irregular cluster, on short to long stems, of normal strength. The plant blooms very abundantly outdoors, in Ontario, Calif., and nearly continuously during the growing season. It has a slight fragrance, between musk and tea.

This new cultivar is distinguishable from its seed parent, Folie d'Espagne, in the following ways:

Whereas the flowers on the new cultivar are normally from 3 to 3¼ inches in diameter, the flowers of the seed parent generally are about 2 inches in diameter.

Folie d'Espagne usually has about 20 petals, while this new cultivar has significantly more—namely, from 55 to 70 petals, plus petaloids.

The pollen parent of this new cultivar is an unnamed, undisseminated seedling which resulted from a cross of Zambra × Danish Pink. This new cultivar differs from these two parents of its pollen parent in the following ways:

The flowers of Zambra are smaller than the flowers of this new cultivar, i.e., from 2½ to 3 inches in diameter as compared to 3 to 3¼ inches in diameter. Whereas the number of petals found in the flowers of the new cultivar is between 55 and 70, the petal count of Zambra is only from 10 to 15. The color of the blooms of Zambra is described as "nasturtium-orange with a yellow reverse" (Modern Roses 7), whereas the new cultivar opens pure orange and becomes a blend of orange and pink with small traces of yellow.

The pollen parent of the new cultivar's pollen parent, Danish Pink, has flowers which are from 2 to 2½ inches in diameter as compared to the from 3 to 3¼ inch flowers of the new cultivar. Danish Pink is nearly single, whereas the new cultivar is fully double, with from 5 to 10 times more petals. Danish Pink is deep pink in color; the new cultivar opens orange and becomes a blend of orange, pink and yellow.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Company.

BUD

The peduncle is from average length to long, of average caliper, erect, and having numerous stipitate glands. The color is between Strong Yellow Green, 5GY/10, and Strong Yellow Green, 5GY6/8, sometimes lightly overlaid with near Dark Red, 2.5R3/7.

Before the calyx breaks, the bud is small in size, short and nearly globular, with small foliaceous appendages and some stipitate glands on the surface of the bud. Usually, slender foliaceous parts extend beyond the tip of the bud for a distance equal to at least three-fourths of its length.

As the calyx breaks, the color is between Strong Yellowish Pink, 10R7/9, and Strong Reddish Orange, 7.5R6/12. The inner surface of the sepals carries a fine, wooly tomentum.

Margins developing on the exterior of the bud have stipitate glands and long slender foliaceous appendages; margins developing under overlapping sepals have stipitate glands and fine hairs. The outside surface of the sepals carries some stipitate glands.

As the first petal opens, the bud is small in size, short to medium-length, and from globular to urn-shaped. The color on the outside of the petal is near Strong Orange, 2.5YR7/10, with a basal area near Vivid Yellow, 2.5Y8/12. The inside surface of the petal is between Strong Orange, 5YR7/11, and Strong Yellowish Pink, 7.5R7/9, with a basal area near Vivid Yellow, 5Y8/12. The bud opens up well, and is not retarded or prevented from opening by cold, hot, wet, or dry weather.

BLOOM

When fully open, the bloom is from small to average for its class, being from 3 to 3¼ inches. The petalage is very double, with from 55 to 70 petals arranged irregularly, plus from 8 to 16 petaloids. The bloom is cupped and full at first, becoming open and full.

At first the petals remain somewhat cupped, becoming later, at maturity, loosely cupped, with the petals usually curved outward. The petal arrangement is informal, irregular.

The petals are of medium thickness, moderately soft, with the inside slightly shiny to dull. The outside of the petals is slightly shiny to satiny. Both the outside and intermediate petals are obovate and mucronate in shape. The inside petals are narrowly obovate to irregular, with apex notched irregularly. The colors may be modified by being striped, shaded and/or washed or tinted, with other colors.

The paragraphs immediately following describe color values observed in a flower newly opened in the month of August. The plant had been grown outdoors, in Ontario, Calif.

The outer surface of the outside petal is near Vivid Yellow, 5Y8/12, at the base, blending to between Light Orange, 2.5YR8/6, and Strong Orange, 2.5YR7/10, in apical half of the petal, with some shading of near Deep Pink, 2.5R6/11, near the apex of the petal. The inner surface of the outside petal is near Vivid Yellow, 5Y8/12, at the base, becoming between Strong Orange, 2.5YR7/10, and Strong Yellowish Pink, 10R7/9, throughout the main surface area of the petal.

The outer surface of the intermediate petal is near Vivid Yellow, 5Y8/12, at the base, blending to near Strong Orange, 2.5YR7/10, in apical half of the petal. The inner surface of the intermediate petal is near Vivid Yellow, 2.5Y8/12, at the base, becoming a color between Strong Orange, 2.5YR7/10, and Strong Orange, 2.5YR6/12.

Both the outer surface and the inner surface of the inner petal are of the same coloration as the intermediate petals.

The paragraphs immediately following describe the color values observed in a bloom which had been open for three days, outdoors, in the month of August. The plant had been grown in Ontario, Calif.

The outer surface of the outside petal is near Vivid Yellow, 5Y8/12, at the base, and extending out to one-third of the petal length as pale yellow and blending to near Moderate Pink, 5R8/6, along the marginal one-third of the petal. The inner surface of the outside petal is near Vivid Yellow, 5Y8/12, at the base, blending Yellowish Pink, 5R7/9, in the marginal one-third of the petal.

The outer surface of the inside petal is near Vivid Yellow, 5Y8/12, at the base, blending through pale yellow to between Moderate Yellowish Pink, 7.5R8/6, and Strong Yellowish Pink, 7.5R7/9, in the marginal or outer half of the petal. The inner surface of the inside petal is near Vivid Yellow, 5Y8/12, at the base, blending to between Strong Yellowish Pink, 7.5R7/9, and Strong Reddish Orange, 7.5R6/12, in apical half of the petal.

The general color effect of the newly opened flower is between Strong Orange, 2.5YR7/10, and Strong Orange, 2.5YR6/12. After being three days open, the bloom gives a general color effect which is between Strong Reddish Orange, 7.5R6/12, and Deep Yellowish Pink, 5R6/11. The petals drop off cleanly, except for petaloids, and are not particularly affected by cold, hot, wet, or dry weather.

The flower on the bush in the garden persists from 4 to 5 days in the month of August, in the locality named. Cut roses grown outdoors and kept at living-room temperatures will last from 3 to 4 days in the month of August.

REPRODUCTIVE ORGANS

Stamens: The stamens are average in number, arranged regularly about the pistils, a few being mixed with petaloids and a few tucked in the calyx.

Filaments: The filaments are medium length to long, being ¼ to ⅜ inch in length, and near Vivid Yellow, 5Y8/12, in color. Most are with anthers.

Anthers: The anthers are very small, all opening approximately at once. On both the upper and lower side the margins are near Strong Orange Yellow, 7.5YR7/11, in color, while the interior is light yellow.

Pollen: Pollen is from sparse to moderate, and near Strong Orange Yellow, 7.5YR7/11, in color.

Pistils: There are approximately 75 pistils, this being average.

Styles: The styles are from even to uneven, short to average length, and average caliper. They are somewhat loosely bunched.

Stigma: The stigma is between Brilliant Greenish Yellow, 7.5Y9/8, and Brilliant Yellow, 5Y9/9, in color, on newly opened flowers.

Ovaries: Usually, most of the ovaries are enclosed in the Calyx.

Hips: Hips are of average length and globular to somewhat pear-shaped, with a flattened or somewhat depressed apex. At three-fourths maturity the color is between Strong Yellow Green, 2.5GY6/8, and Moderate Yellow Green, 2.5GY5/5, and they are smooth, with thick and fleshy walls.

Sepals: Sepals are sometimes permanent, but usually falling soon. They are medium-length and recurved. From a half-mature hip, the inside color of persistent sepals was either near Moderate Yellow Green, 7.5GY5/7, overlaid with gray tomentum, or dead and between grayish tan and dark brownish gray. The outside coloration was the same as the inside, except without the gray tomentum.

Seeds: There were an average number of seeds, from 15 to 30, usually from small to medium size.

FOLIAGE

The compound leaves usually comprise three to seven leaflets, which is normal. They are small to medium in size, for this class, moderately heavy to somewhat leathery, and glossy. The leaflets are ovate, with apex acute to acuminate, the base round, and the margin from doubly to irregularly serrate.

The mature foliage displays upon its upper surface a color between Moderate Olive Green, 2.5GY4/3, and Grayish Olive Green, 2.5GY3/1. The undersurface is more gray than a color near Moderate Yellow Green, 5GY5/6.

The young foliage on its upper surface is between Strong Yellow Green, 5GY6/8, and Moderate Yellow Green, 5GY5/6, moderately overlaid near the margins with near Dark Red, 5R3/7; the undersurface being between Strong Yellow Green, 5GY7/10, and Strong Yellow Green, 5GY6/8, and lightly to heavily overlaid, especially near the margins, with near Dark Red, 5R3/7.

The rachis is average in size, the upper side being grooved, with many stipitate glands on the edges. The underside is sparsely prickly, and with stipitate glands.

The stipules are medium-length to long, narrow, with very narrow, short to medium-length points turning out at an angle of more than 45°.

The plant displays a more than average resistance to mildew, when compared with other commercialized cultivars grown under comparable conditions, at Ontario, Calif.

GROWTH

The plant is upright, bushy, and moderately branched. Its growth is vigorous. The canes are of medium caliper.

The main stems are a color ranging from a grayish brown to between Dark Greenish Yellow, 10Y6/7, and Light Olive, 10Y5/5. They bear several large prickles which are medium-length to long, hooked slightly downward, and with medium-length, moderately narrow base. The color of the large prickles is between gray and Strong Brown, 5YR4/5. There are very few small prickles, and their color is the same as the large prickles. There are no hairs.

The branches are a color between Strong Yellow Green, 2.5GY6/8, and Moderate Yellow Green, 2.5GY5/5. They carry from few to several large prickles which are medium-length to long, hooked slightly downward, and with medium-length, moderately narrow base. The color is generally between Strong Brown, 5YR4/5, and Moderate Brown, 7.5YR4/5. There are very few small prickles, and these are the same color as the large prickles. There are no hairs.

New shoots have a color near Strong Yellow Green, 5GY6/8, overlaid lightly to heavily, depending on exposure to sunlight, with near Dark Red, 2.5R3/7. There are several large prickles which are medium-length to long, hooked slightly downward, with medium-length to long, narrow base. There are from none to few small prickles, and both the large and small prickles were the same color as the new shoots. There were from none to many stipitate glands, but no hairs.

I claim:

1. An asexually reproduced rose plant of the grandiflora class substantially as herein illustrated and described, being especially characterized in that the flower has a strong orange color when freshly opened, yielding later to an orange pink, tinged with yellow and red, the plant further having in combination, a plurality of the following features, namely, the bush is of an upright moderately branched and spreading habit, has glossy foliage with relatively small leaves, and produces buds which are nearly globular, generally in clusters of three to five on each stem; which buds open to produce flowers of about 3 inches in diameter with double petalage of 55 to 70 petals, of obovate and mucronate shapes, plus 8 to 16 petaloids, the bloom having a fragrance of musk to tea, said plant blooming almost continuously during the growing season.

No references cited.

ROBERT E. BAGWILL, Primary Examiner

UNITED STATES PATENT OFFICE

CERTIFICATE OF CORRECTION

Patent No. PP 3794 Dated October 14, 1975

Inventor(s) Olaf Soenderhousen

It is certified that error appears in the above-identified patent and that said Letters Patent are hereby corrected as shown below:

Column 2, line 12 - "5GY/10" should be --5GY7/10--

Column 3, line 19 - at the beginning of the line, before "Yellowish Pink", insert --through Strong Yellowish Pink, 7.5R7/9, to near Strong--

Signed and Sealed this

*thirteenth* Day of *April 1976*

[SEAL]

*Attest:*

RUTH C. MASON
*Attesting Officer*

C. MARSHALL DANN
*Commissioner of Patents and Trademarks*